(12) United States Patent
Kitagawa et al.

(10) Patent No.: US 12,338,347 B2
(45) Date of Patent: Jun. 24, 2025

(54) MEDICAL DEVICE

(71) Applicant: TORAY Industries, Inc., Tokyo (JP)

(72) Inventors: Rumiko Kitagawa, Otsu (JP);
Masataka Nakamura, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 624 days.

(21) Appl. No.: 17/289,560

(22) PCT Filed: Dec. 5, 2019

(86) PCT No.: PCT/JP2019/047629
§ 371 (c)(1),
(2) Date: Apr. 28, 2021

(87) PCT Pub. No.: WO2020/121941
PCT Pub. Date: Jun. 18, 2020

(65) Prior Publication Data
US 2021/0395526 A1 Dec. 23, 2021

(30) Foreign Application Priority Data
Dec. 12, 2018 (JP) .................................. 2018-232198

(51) Int. Cl.
| | | |
|---|---|---|
| *C08L 83/04* | (2006.01) | |
| *A61L 15/24* | (2006.01) | |
| *A61L 15/26* | (2006.01) | |
| *A61L 26/00* | (2006.01) | |
| *A61L 27/16* | (2006.01) | |
| *A61L 27/18* | (2006.01) | |
| *A61L 27/50* | (2006.01) | |
| *A61L 29/04* | (2006.01) | |
| *A61L 29/06* | (2006.01) | |
| *A61L 29/14* | (2006.01) | |
| *A61L 31/04* | (2006.01) | |
| *A61L 31/06* | (2006.01) | |
| *A61L 31/14* | (2006.01) | |
| *C08L 33/08* | (2006.01) | |
| *G02B 1/04* | (2006.01) | |
| *G02C 7/04* | (2006.01) | |

(52) U.S. Cl.
CPC ............. *C08L 83/04* (2013.01); *A61L 15/24* (2013.01); *A61L 15/26* (2013.01); *A61L 26/0014* (2013.01); *A61L 26/0019* (2013.01); *A61L 27/16* (2013.01); *A61L 27/18* (2013.01); *A61L 27/50* (2013.01); *A61L 29/041* (2013.01); *A61L 29/06* (2013.01); *A61L 29/14* (2013.01); *A61L 31/048* (2013.01); *A61L 31/06* (2013.01); *A61L 31/14* (2013.01); *C08L 33/08* (2013.01); *G02B 1/043* (2013.01); *G02C 7/049* (2013.01); *A61L 2400/10* (2013.01); *A61L 2430/16* (2013.01)

(58) Field of Classification Search
CPC ......... C08L 83/04; C08L 33/08; G02B 1/043; G02C 7/049; A61L 26/0014; A61L 27/16; A61L 29/041; A61L 15/24; A61L 31/048; A61L 15/26; A61L 26/0019; A61L 31/14; A61L 29/14; A61L 27/18; A61L 29/06; A61L 31/06; A61L 27/50; A61L 2400/10; A61L 2430/16
See application file for complete search history.

(56) References Cited

U.S. PATENT DOCUMENTS

| | | | |
|---|---|---|---|
| 7,396,890 B2 * | 7/2008 | Zanini | G02B 1/043 526/307.7 |
| 2003/0162862 A1 | 8/2003 | McCabe et al. | |
| 2006/0276608 A1 * | 12/2006 | Lang | G02B 1/043 524/916 |
| 2008/0275156 A1 | 11/2008 | Laredo et al. | |
| 2014/0240660 A1 | 8/2014 | Fujisawa et al. | |
| 2015/0274854 A1 | 10/2015 | Tamiya et al. | |
| 2017/0204213 A1 * | 7/2017 | Kato | A61L 27/52 |
| 2019/0187332 A1 | 6/2019 | McCabe et al. | |
| 2020/0139653 A1 | 5/2020 | Kitagawa et al. | |

FOREIGN PATENT DOCUMENTS

| | | |
|---|---|---|
| CN | 106459309 A | 2/2017 |
| JP | 2005-518826 A | 6/2005 |
| JP | 2008-519907 A | 8/2006 |
| JP | 2008-514799 A | 5/2008 |
| JP | 2009-185302 A | 8/2009 |
| JP | 2009-204770 A | 9/2009 |
| JP | 2010-15175 A | 1/2010 |
| JP | 2017-23374 A | 2/2017 |
| WO | WO 2004/081105 A2 | 9/2004 |
| WO | WO 2015/198919 A1 | 12/2015 |
| WO | WO 2018/207644 A1 | 11/2018 |

OTHER PUBLICATIONS

International Search Report, issued in PCT/JP2019/047629, dated Mar. 3, 2020.

(Continued)

*Primary Examiner* — Patrick D Niland
(74) *Attorney, Agent, or Firm* — Birch, Stewart, Kolasch & Birch, LLP

(57) ABSTRACT

A medical device including an internal wetting agent and a copolymer of a silicone monomer and satisfying the following conditions: (1) that the internal wetting agent contains a copolymer of an open-chain compound having an acidic group and an open-chain compound having an amide group; (2) that the internal wetting agent is contained in the range of from 0.1 to 10% by mass with respect to the whole medical device; and (3) that the copolymer of a silicone monomer has a hydroxyl group and that the content ratio of the hydroxyl group in the silicone monomer is in the range of from 0.0005 to 0.01 equivalents/g. A medical device containing an internal wetting agent and having excellent transparency and hydrophilicity can be obtained.

8 Claims, No Drawings

(56) References Cited

OTHER PUBLICATIONS

Written Opinion of the International Searching Authority, issued in PCT/JP2019/047629, dated Mar. 3, 2020.
Extended European Search Report for European Application No. 19897487.5, dated May 27, 2022.

\* cited by examiner

MEDICAL DEVICE

TECHNICAL FIELD

The present invention relates to a medical device which contains an internal wetting agent, is transparent, and has excellent hydrophilicity.

BACKGROUND ART

There are known those biomedical devices and contact lenses which do not need surface treatment, can be manufactured more easily, and contain an internal wetting agent (water absorbing agent). For example, when a biomedical device is introduced into a living body as a medical device or attached to a surface of a living body, the surface hydrophilicity of the medical device is important for the purpose of improving biocompatibility. If an internal wetting agent can impart good properties such as hydrophilicity, lubricity, and biocompatibility to the medical device, users (patients, etc.) can expect an improvement in tactile sensation, reduction of discomfort, a symptomatic improvement, and the like.

Various methods have been known as methods for imparting hydrophilicity to a medical device using an internal wetting agent.

CITATION LIST

Patent Literature

For example, Patent Literature 1 discloses a biomedical device containing: 1 to 15% by mass of a hydrophilic polylactam having a weight average molecular weight of 100,000 daltons or more; and 28 to 68% by mass of a silicone-containing monomer having a hydroxyl group.

Furthermore, Patent Literature 2 discloses a biomedical device containing: 1 to 15% by mass of a polyvinyl compound having a lactam pendant group and having a weight average molecular weight of 100,000 daltons or more; and 28 to 68% by mass of a hydroxyl-functionalized silicone-containing monomer.

In addition, Patent Literature 3 discloses a composition containing at least one silicone-containing component, at least one hydrophilic component, a high molecular weight hydrophilic polymer, and a diluent.

In addition, Patent Literature 4 discloses a composition containing at least one silicone-containing component, at least one hydrophilic component, a high molecular weight hydrophilic polymer, and a diluent.

Patent Literature 1: JP 2005-518826 W
Patent Literature 2: JP 2010-015175 A
Patent Literature 3: JP 2006-519907 W
Patent Literature 4: JP 2009-185302 A

SUMMARY OF INVENTION

Technical Problem

However, such a biomedical device as described in Patent Literature 1 involves limiting a usable internal wetting agent to a hydrophilic polylactam. In addition, such a biomedical device as described in Patent Literature 2 involves limiting a usable internal wetting agent to a polyvinyl compound having a lactam pendant group. Furthermore, studying these internal wetting agents has found out a problem in that a long time is taken to dissolve 15% by mass of such an internal wetting agent to produce a reaction mixture as a basis for a biomedical device. Manufacturing time made longer involves increasing utility costs and labor costs. This will undesirably increase manufacturing costs.

Studying such compositions as described in Patent Literature 3 and 4 has found out that the compositions have a problem with transparency, for example, in applications to a medical device such as an ophthalmic lens.

The present invention has been made in view of the aforementioned problems of background art. That is, an object of the present invention is to provide a medical device containing an internal wetting agent and having excellent transparency and water wettability.

Solution to Problem

To achieve the above object, the present invention has the following structures.

That is, a medical device including an internal wetting agent and a copolymer of a silicone monomer and satisfying the following conditions:

(1) that the internal wetting agent contains a copolymer of an open-chain compound having an acidic group and an open-chain compound having an amide group;

(2) that the internal wetting agent is contained in the range of from 0.1 to 10% by mass with respect to the whole medical device; and (3) that the copolymer of a silicone monomer has a hydroxyl group and that the content ratio of the hydroxyl group in the silicone monomer is in the range of from 0.0005 to 0.01 equivalents/g.

Advantageous Effects of Invention

According to the present invention, unlike background art, it is possible to obtain a medical device containing an internal wetting agent and having excellent transparency and hydrophilicity. In addition, the amount of a usable internal wetting agent is in the range of from 0.1 to 10% by mass, and thus, such a smaller amount of internal wetting agent enables the above-mentioned properties to be imparted.

DESCRIPTION OF EMBODIMENTS

The present invention relates to a medical device including an internal wetting agent and a copolymer of a silicone monomer.

In the present invention, an internal wetting agent is a chemical substance contained in a raw material composition of a medical device, and refers to a chemical substance which makes it possible that the hydrophilicity and/or wettability of the medical device obtained from the raw material composition is improved compared with a control medical device obtained from a control raw material composition containing no internal wetting agent.

The internal wetting agent plays a role as a water absorbing agent. The internal wetting agent playing a role as a water absorbing agent in a medical device is constituted by a material having hydrophilicity. Here, the material having hydrophilicity is a material which is soluble in 100 parts by mass of water at room temperature (20 to 23° C.) in an amount of 0.0001 part by mass or more, preferably 0.01 part by mass or more, more preferably 0.1 part by mass or more, and particularly preferably 1 part by mass or more, based on 100 parts by mass of water.

An internal wetting agent to be used for the present invention contains a copolymer of an open-chain compound having an acidic group and an open-chain compound having an amide group. Having an acidic group and an amide group causes the internal wetting agent to exhibit a suitable viscosity when dissolved in water, and thus, enables water wettability and lubricity to be imparted to the medical device.

In addition, the internal wetting agent which is a copolymer of open-chain compounds results in having excellent compatibility with a silicone monomer having an acidic group, and thus, has an advantage in handling from a manufacturing viewpoint. As used herein, an open-chain compound means a compound having a molecular structure which is linear and has no ring. In some cases, an open-chain compound is referred to as an acyclic compound. As used herein, an acidic group specifically means a group selected from a carboxy group and a sulfonic group. Among these, a carboxy group is particularly preferable. The acidic group may be in the form of a salt.

Examples of the open-chain compound having an acidic group include methacrylic acids, acrylic acids, vinylsulfonic acids, 2-acrylamido-2-methylpropanesulfonic acid, and salts thereof. Compounds selected from (meth)acrylic acids and salts thereof are particularly preferable.

In view of ease of polymerization, preferable examples of the open-chain compound having an amide group include compounds selected from: compounds having a (meth)acrylamide group; and N-vinylcarboxylic acid amide (not including cyclic compounds). Suitable Examples of such compounds include N-vinylacetamide, N-methyl-N-vinylacetamide, N-vinylformamide, N,N-dimethylacrylamide, N,N-diethylacrylamide, N-isopropylacrylamide, N-(2-hydroxyethyl)acrylamide, and acrylamide. Of these, N,N-dimethylacrylamide or N,N-diethylacrylamide is preferable in view of the lubricity, and N,N-dimethylacrylamide is particularly preferable.

The copolymer of an open-chain compound having an acidic group and an open-chain compound having an amide group is a copolymer containing, as monomer units, the above-mentioned open-chain compound having an acidic group and the above-mentioned open-chain compound having an amide group. Preferred specific examples of the copolymer of an open-chain compound having an acidic group and an open-chain compound having an amide group include a (meth)acrylic acid/N,N-dimethylacrylamide copolymer, a (meth)acrylic acid/N,N-diethylacrylamide copolymer, a 2-acrylamide-2-methylpropanesulfonic acid/N,N-dimethylacrylamide copolymer, and a 2-acrylamide-2-methylpropanesulfonic acid/N,N-diethylacrylamide copolymer. A (meth)acrylic acid/N,N-dimethylacrylamide copolymer is particularly preferable.

For the copolymer of an open-chain compound having an acidic group and an open-chain compound having an amide group, the copolymerization ratio of the compounds is preferably in the range of from 1/99 to 99/1 in terms of [mass of monomer unit having an acidic group]/[mass of monomer unit having an amide group]. The copolymerization ratio of the open-chain compound having an acidic group is more preferably 2% by mass or more, still more preferably 5% by mass or more, yet more preferably 7% by mass or more, and even more preferably 10% by mass or more. The copolymerization ratio of the open-chain compound having an acidic group is more preferably 90% by mass or less, still more preferably 80% by mass or less, and yet more preferably 70% by mass or less. The copolymerization ratio of the open-chain compound having an amide group is more preferably 10% by mass or more, still more preferably 20% by mass or more, and yet more preferably 30% by mass or more. The copolymerization ratio of the open-chain compound having an amide group is more preferably 98% by mass or less, still more preferably 95% by mass or less, yet more preferably 93% by mass or less, and even more preferably 90% by mass or less. When the copolymerization ratios of the open-chain compound having an acidic group and the open-chain compound having an amide group are in the above range, it becomes easy to develop functions such as lubricity and antifouling properties against body fluid.

In addition, it is possible to copolymerize two or more kinds of open-chain compounds having an acidic group and/or two or more kinds of open-chain compounds having an amide group. It is also possible to copolymerize one or more kinds of open-chain compounds having neither acidic group nor amide group.

Suitable examples of open-chain compounds other than above-mentioned include hydroxyethyl (meth)acrylate, hydroxypropyl (meth)acrylate, hydroxybutyl (meth)acrylate, glycerol (meth)acrylate, and vinyl alcohol (carboxylic acid vinyl ester as a precursor). Of these, in view of ease of polymerization, an open-chain compound having a (meth)acryloyl group is preferable and a (meth)acrylic acid ester is more preferable. Of these, in view of improving antifouling properties against body fluid, hydroxyethyl (meth)acrylate, hydroxypropyl (meth)acrylate, and glycerol (meth)acrylate are preferable, and hydroxyethyl (meth)acrylate is particularly preferable. It is also possible to use an open-chain compound having functions such as hydrophilicity, antibacterial properties, antifouling properties, and medicinal effects.

When a copolymer of an open-chain compound having an acidic group and an open-chain compound having an amide group is copolymerized with a third monomer component which is an open-chain compound having neither acidic group nor amide group, the copolymerization ratio of the third monomer component is more preferably 2% by mass or more, still more preferably 5% by mass or more, and yet more preferably 10% by mass or more. The copolymerization ratio of the third monomer component is more preferably 90% by mass or less, still more preferably 80% by mass or less, and yet more preferably 70% by mass or less.

If the copolymerization ratios of the monomer having an acidic group, the monomer having an amide group, and the third monomer component are in the above range, functions such as lubricity and antifouling properties against body fluid are easily developed.

The internal wetting agent to be contained in a medical device of the present invention may be one kind of copolymer of the above-mentioned open-chain compounds, or may be a mixture of two or more kinds of copolymers of the open-chain compounds. However, this tends to complicate the manufacturing method, and thus, the internal wetting agent is preferably one kind of copolymer of an open-chain compound having an acidic group and an open-chain compound having an amide group.

Here, one kind of copolymer means a copolymer (encompassing isomers, complexes, etc.) produced by one synthesis reaction. Even though the constituent monomers are of the same species, copolymers synthesized with varying compounding ratios of the monomers are not said to be copolymers of the same one kind.

In addition, it is possible to further contain a known internal wetting agent other than an internal wetting agent of the copolymer of open-chain compounds, but in this case, the amount of the other internal wetting agent is preferably 3 parts by mass or less with respect to 100 parts by mass of the copolymer of an open-chain compound having an acidic group and an open-chain compound having an amide group. The amount of the other internal wetting agent is more preferably 0.1 part by mass or less, and still more preferably 0.0001 part by mass or less.

Increasing the amount of the internal wetting agent in a medical device generally enhances the hydrophilicity of the obtained medical device. However, too large an amount of internal wetting agent increases the viscosity, and can increase the difficulty of handling during manufacturing and decrease transparency. The amount of the internal wetting agent contained in the medical device is preferably 0.1% by mass to 10% by mass with respect to the whole medical device. The amount of the internal wetting agent is more preferably 2% by mass or more, still more preferably 3% by mass or more. In addition, the amount of the internal wetting agent is more preferably 8% by mass or less, still more preferably 6% by mass or less.

The internal wetting agent preferably has a molecular weight of 2,000 to 1,000,000. The molecular weight is preferably 50,000 or more, more preferably 100,000 or more, and still more preferably 200,000 or more, from the viewpoint of exhibiting sufficient water wettability and lubricity. The molecular weight is preferably 900,000 or less, more preferably 800,000 or less, and still more preferably 700,000 or less. Here, a mass average molecular weight in terms of polyethylene glycol measured by a gel permeation chromatography method (aqueous solvent) is used as the molecular weight.

The medical device of the present invention includes a copolymer of a silicone monomer having a hydroxyl group. The silicone monomer containing a hydroxyl group in too large or too small an amount makes it more difficult to obtain a transparent medical device, and thus, at least one kind of silicone monomer preferably has a hydroxyl group in an amount of 0.0005 to 0.01 equivalents/g, more preferably 0.0008 to 0.008 equivalents/g, still more preferably 0.001 to 0.005 equivalents/g. The amount of the hydroxyl group in the silicone monomer can be determined by identifying the structure of the silicone monomer having the hydroxyl group using any one of the various analysis methods such as gas chromatography-mass spectrometry (GC-MS), high performance liquid chromatography-mass spectrometry (HPLC-MS), nuclear magnetic resonance (NMR), and infrared spectroscopy (IR).

Suitable examples of silicone monomers used for the medical device of the present invention include silicone monomers of the following formulae (a) and (b).

[Chemical Formula 1]

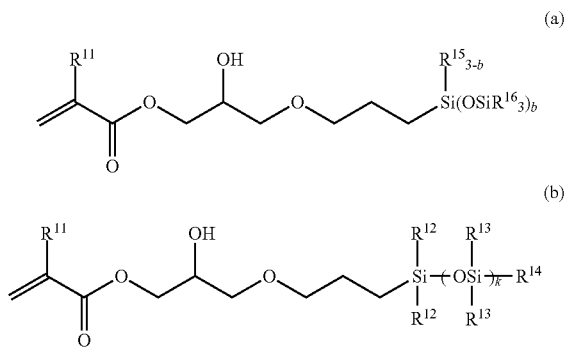

In the formulae (a) and (b), k represents an integer of 0 to 100. b represents an integer of 1 to 3.

$R^{11}$ represents H or a methyl group.

$R^{12}$ and $R^{13}$ independently represent a substituent selected from $C_{1-18}$ alkyl groups and phenyl groups.

$R^{14}$ represents a substituent selected from $C_{1-6}$ alkyl groups and phenyl groups.

$R^{15}$ and $R^{16}$ independently represent a substituent selected from $C_{1-18}$ alkyl groups and phenyl groups.

A larger integer as k enhances the oxygen permeability of the resulting medical device, and a smaller integer as k tends to make it easier to obtain a transparent medical device. k is more preferably 1 to 30, still more preferably 1 to 20, still more preferably 2 to 10. Too small an integer as b decreases the oxygen permeability of the resulting medical device, and too large an integer as b tends to make the elastic modulus too high. b is preferably 2 or 3.

$R^{11}$ is preferably a methyl group from the viewpoint of the chemical stability of the resulting medical device.

$R^{12}$ and $R^{13}$ are preferably $C_{1-4}$ alkyl groups, more preferably methyl groups, from the viewpoint of obtaining a polymer having higher oxygen permeability.

$R^{14}$ is preferably a $C_{1-4}$ alkyl group from the viewpoint of obtaining a polymer having higher oxygen permeability, and more preferably a methyl group or butyl group, additionally considering the ease of manufacturing.

$R^{15}$ are $R^{16}$ are preferably $C_1$ or $C_4$ alkyl groups from the viewpoint of obtaining a polymer having higher oxygen permeability, and more preferably methyl groups, additionally considering the ease of manufacturing.

The medical device of the present invention may be based on copolymerizing another monomer besides the silicone monomer. Examples of the another monomer to be suitably used for copolymerization include monomers having a group selected from (meth)acryloyl groups, styryl groups, allyl groups, and vinyl group.

Some examples thereof are as follows: carboxylic acids such as (meth)acrylic acids, itaconic acids, crotonic acids, and vinylbenzoic acids; alkyl (meth)acrylates such as methyl (meth)acrylate; (meth)acrylates having a hydroxyl group, such as 2-hydroxyethyl (meth)acrylate and glycerol (meth) acrylate; (meth)acrylamides such as N,N-dimethylacrylamide; and aromatic vinyl monomers such as styrene.

Among these, monomers having a (meth)acryloyl group are preferable, and (meth)acryloyl group-containing monomers having a hydroxyl group, such as 2-hydroxyethyl (meth)acrylate, are particularly preferable, from the viewpoint of the higher ease of obtaining a transparent medical device. The amount of the (meth)acryloyl group-containing monomer having a hydroxyl group is preferably 0.1 to 55% by mass, more preferably 5 to 50% by mass, still more preferably 10 to 45% by mass, with respect to the whole medical device, because the monomer used in too small an amount makes it more difficult to obtain a transparency enhancing effect, and the monomer used in too large an amount affects the physical properties of the polymer.

For the medical device of the present invention, any alkyl (meth)acrylate is preferably used as a copolymerization component in addition to the above-mentioned (meth)acryloyl group-containing monomer having a hydroxyl group, from the viewpoint of obtaining good flexibility and bending resistance in addition to transparency. The amount of an alkyl (meth)acrylate is preferably 0.1% by mass to 30% by mass, more preferably 0.3% by mass to 20% by mass, still more preferably 0.5% by mass to 25% by mass, with respect to the whole medical device, from the viewpoint of good flexibility and bending resistance.

Suitable examples of alkyl (meth)acrylates include (meth) acrylic acid alkyl esters, preferably (meth)acrylic acid alkyl esters in which the alkyl group has 1 to 20 carbon atoms. Specific example of (meth)acrylic acid alkyl esters include: methyl (meth)acrylate, ethyl (meth)acrylate, n-propyl (meth)acrylate, n-butyl (meth)acrylate, tert-butyl (meth) acrylate, isobutyl (meth)acrylate, n-hexyl (meth)acrylate, n-octyl (meth)acrylate, 2-ethylhexyl (meth)acrylate, n-heptyl (meth)acrylate, n-nonyl (meth)acrylate, n-decyl (meth) acrylate, isodecyl (meth)acrylate, n-lauryl (meth)acrylate, tridecyl (meth)acrylate, n-dodecyl (meth)acrylate, cyclopentyl (meth)acrylate, cyclohexyl (meth)acrylate, and n-stearyl (meth)acrylate; more preferably n-butyl (meth)acrylate, n-octyl (meth)acrylate, n-lauryl (meth)acrylate, and n-stearyl (meth)acrylate. Among these, (meth)acrylic acid alkyl esters in which the alkyl group has 1 to 10 carbon atoms are more preferable. The alkyl group having too large a carbon number causes the tensile elongation of the medical device to decrease, thus embrittling the copolymer in some cases, and thus is not preferable.

From the viewpoint of controlling the manufacturing costs, the internal wetting agent and the copolymer of a silicone monomer preferably have no covalent bond therebetween. In this case, it is preferable that the internal wetting agent is uniformly and optically mixed in the copolymer of a silicone monomer without being fixed via a covalent bond. Additionally in this case, it is preferable that the molecules of the internal wetting agent are sufficiently entwined around the molecules of the copolymers of a silicone monomer, and are not eluted under usual conditions of use.

The medical device of the present invention may further contain a UV absorber, pigment, colorant, or the like. In addition, such a UV absorber, pigment, or colorant may have a polymerizable group and be in copolymerized form.

The medical device of the present invention may have a lens shape and is preferably an ophthalmic lens. Specific examples thereof include ophthalmic lenses such as contact lens, intraocular lens, artificial cornea, corneal inlay, corneal onlay, and eyeglass lens.

The medical device of the present invention may be in the form of a tube. Examples of a tubular device include an infusion tube, a gas delivery tube, a drainage tube, a blood circuit, a coating tube, a catheter, a stent, a sheath, a tube connector, an access port, and the like.

The medical device of the present invention may be in the form of a sheet or a film. Specific examples thereof include a dermal covering material, a wound dressing material, a skin protection material, a skin medicine carrier, a biosensor chip, an endoscopic dressing material, and the like.

The medical device of the present invention may have a storage container shape. Specific examples thereof include a medicine carrier, a cuff, a drainage bag, and the like.

An ophthalmic lens, especially a contact lens, is one of most preferred embodiments of the present invention.

The moisture content of the medical device is preferably 5% by mass or more, and particularly preferably 10% by mass or more. In addition, the moisture content of the medical device is preferably 60% by mass or less, more preferably 50% by mass or less, and still more preferably 40% by mass or less.

When the medical device is a contact lens, since it is easy to ensure the movement of the lens in eyes, the moisture content of the medical device is preferably 15% by mass or more, and sill more preferably 18% by mass or more.

The medical device of the present invention preferably contains silicon atoms at a ratio in the range of from 5 to 30% by mass with respect to the dry mass of the medical device. Here, the content ratio of silicon atoms with respect to the dry mass of the medical device can be measured using an inductively coupled plasma (ICP) emission spectrophotometer (suitably a sequential type ICP emission spectrophotometer, SPS4000, manufactured by Seiko Instruments Inc.). The measurement method is as below-mentioned.

First, a medical device is brought in a dry state. In the present invention, the medical device being in a dry state refers to a medical device which has been subjected to vacuum drying at 40° C. for two hours. The degree of vacuum in the vacuum drying is set to 2 hPa or less. The medical device (4 to 5 mg) in a dry state is weighed out into a platinum pot, supplemented with sulfuric acid, and heated using a hot plate and a burner to be ashed. The resulting calcareous material is melted with sodium carbonate, supplemented with water, heated to be dissolved, supplemented with nitric acid, and then supplemented with water to make up a given volume. The resulting solution is measured for silicon atoms using an ICP emission spectral analysis method, and the content ratio of silicon atoms in the medical device is calculated.

Too small a content ratio of silicon atoms in the medical device will cause the oxygen permeability to decrease, and the content ratio which is too large will make it more difficult to obtain a transparent medical device. Thus, the content ratio is preferably 5 to 30% by mass. In addition, the content ratio of silicon atoms is more preferably 7 to 27% by mass, more preferably 10 to 25% by mass, still more preferably 10 to 20% by mass.

In obtaining the medical device of the present invention through polymerization, a thermal polymerization initiator or photopolymerization initiator typified by a peroxide or an azo compound is preferably added to the raw material composition to facilitate the polymerization. In the case of thermal polymerization, a thermal polymerization initiator having the decomposition properties optimal for a desired reaction temperature is selected for use. In general, an azo-based initiator and a peroxide-based initiator which have a 10-hour half-life temperature of 40° C. to 120° C. are suitable. Examples of photopolymerization initiators include carbonyl compounds, peroxides, azo compounds, sulfur compounds, halogen compounds, and metal salts. These polymerization initiators are used singly or in mixture, and used in an amount of up to approximately 1% by mass.

In obtaining the medical device of the present invention through polymerization, a polymerization solvent can be used. As the solvent, any one of various organic and inorganic solvents can be used. Examples thereof include: water; various alcohol-based solvents such as methanol, ethanol, propanol, 2-propanol, butanol, tert-butanol, and tert-amyl alcohol; various aromatic hydrocarbon-based solvents such as benzene, toluene, and xylene; various aliphatic hydrocarbon-based solvents such as hexane, heptane, octane, decane, petroleum ether, kerosene, ligroin, and paraffin; various ketone-based solvents such as acetone, methylethyl ketone, and methylisobutyl ketone; various ester-based solvents such as ethyl acetate, butyl acetate, methyl benzoate, dioctyl phthalate, and ethylene glycol diacetate; various glycol ether-based solvents such as diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether, polyethylene glycol-polypropylene glycol block copolymers, and polyethylene glycol-polypropylene glycol random copolymers. These can be used singly or in mixture. Among these, alcohol-based solvents and glycol ether-based solvents are preferable from the viewpoint of making it possible to easily remove the solvent from the obtained medical device by washing with water.

In cases where the medical device of the present invention is used for an ophthalmic lens, the below-mentioned method can usually be used as a polymerization method or a molding method. Examples thereof include: a method in which a material is once molded in round bar or plate-like shape, and processed into a desired shape by cutting or the like; a mold polymerization method; and a spincast method.

One example in which an ophthalmic lens composed of the medical device of the present invention is of a mold polymerization method will be described below.

A monomer composition is filled into a gap between two molds having a lens shape. The resulting product is subjected to light polymerization or thermal polymerization to obtain a molded body having a lens shape. The mold is made of resin, glass, ceramics, metal, or the like. In light polymerization, an optically transparent material is preferably used, and resin or glass is usually used. In manufacturing a medical device, a gap is often formed between two opposed molds, and a monomer composition is filled into the gap. Subsequently, the molds having the monomer composition filled into the gap are irradiated with active rays such as ultraviolet rays, or placed in an oven or a cistern and heated to polymerize the monomer. Light polymerization can be followed by thermal polymerization, or contrarily thermal polymerization can be followed by light polymerization. Thus, it is possible to use both of them in combination. For light polymerization, for example, it is general that light including a large amount of ultraviolet light from a mercury lamp or an insect collecting light as a light source is used for irradiation in a short time (usually one hour or less). In thermal polymerization, conditions where the temperature is gradually raised from a temperature equal to or near room temperature up to a temperature of 60° C. to 200° C. over a few hours or dozens of hours are preferred to retain the optical uniformity and grade of the polymer and enhance the reproducibility.

As the oxygen permeability of the medical device of the present invention, an oxygen penetration coefficient of $70 \times 10^{-11}$ $(cm^2/sec)mLO_2/(mL \cdot hPa)$ or more is preferable.

The transparency of the medical device of the present invention in applications to ophthalmic lenses is preferably 70% or more, more preferably 80% or more, still more preferably 82% or more, as the total light transmittance of the medical device in a hydrous state from the viewpoint of the grade of the medical device. Details of a method of measuring the total light transmittance will be described later.

When the medical device of the present invention is, for example, a medical device which is used by being attached to a surface of a living body or an ophthalmic device such as an ophthalmic lens, the liquid film retention time on the surface of the medical device is preferably long from the viewpoint of preventing from sticking to the skin of users and preventing from sticking to the cornea of wearers.

A liquid film retention time in the present invention refers to a time during which a liquid film is retained on the surface of the medical device after the medical device is stationarily immersed in a phosphate buffer solution, and pulled up from the phosphate buffer solution so as to be retained in the air. Specifically, when the medical device stationarily immersed in a phosphate buffer solution is pulled up from the solution and retained so that the surface of the medical device can be vertical in the air, the liquid film retention time is from the point of time when the medical device starts being retained so as to be vertical to the point of time when the liquid film of the phosphate buffer solution covering the surface of the device is broken. The expression "the liquid film is broken" means a state where the liquid film on the surface of the medical device can no longer hold the shape, where a phenomenon of repelling a phosphate buffer solution on part of the surface occurs, and where the surface of the medical device becomes no longer covered wholly with the liquid film. The liquid film retention time is preferably 5 seconds or more, more preferably 7 seconds or more, and still more preferably 10 seconds or more.

When the medical device of the present invention is an ophthalmic device such as an ophthalmic lens, the dynamic contact angle of the surface of the medical device is preferably low from the viewpoint of preventing from sticking to the cornea of wearers. The dynamic contact angle is preferably 60° or less, more preferably 55° or less, and particularly preferably 50° or less. The dynamic contact angle (during advancing, immersion rate: 0.1 mm/sec) is measured using a sample wetted with a phosphate buffer solution.

When the medical device of the present invention is a medical device which is used by being inserted into a living body, a surface of the medical device preferably has excellent lubricity. An indicator representing the lubricity, the friction coefficient measured by the method mentioned in Examples of the present specification is preferably small. The friction coefficient is preferably 0.7 or less, more preferably 0.5 or less, and particularly preferably 0.3 or less. If the friction is extremely small, it may be difficult to handle during wearing, so that the friction coefficient is preferably 0.001 or more, and more preferably 0.002 or more.

The tensile elastic modulus of the medical device of the present invention should be appropriately selected according to the type of the medical device. In the case of a soft medical device such as an ophthalmic lens, the tensile elastic modulus is preferably 10 MPa or less, preferably 5 MPa or less, more preferably 3 MPa or less, still more preferably 2 MPa or less, still more preferably 1 MPa or less, and particularly preferably 0.6 MPa or less. The tensile elastic modulus is preferably 0.01 MPa or more, more preferably 0.1 MPa or more, still more preferably 0.2 MPa or more, and still more preferably 0.25 MPa or more. In the case of a soft medical device such as an ophthalmic lens, too small tensile elastic modulus may lead to difficulty in handling because of being excessive in softness. Too large tensile elastic modulus may lead to deterioration of comfort because of being excessive in hardness.

EXAMPLES

The present invention will be described more specifically by way of Examples, but the present invention is not limited to these Examples. First, analytical method and evaluation method will be shown.

<Water Wettability (Liquid Film Retention Time)>

A medical device was left to stand in a storage container at room temperature for 24 hours or more. From the phosphate buffer solution in which the medical device was stationarily immersed, the medical device was pulled up and retained in the air, and the time during which the liquid film was retained on the surface of the medical device was visually observed. Three measurements were taken of the liquid film retention time, and the average of the measurements was judged according to the following criteria. Here, the time during which the liquid film is retained is from the point of time when the medical device starts being retained so as to be vertical in the air to the point of time when the liquid film of the phosphate buffer solution covering the surface of the medical device is broken.

The acceptable level is expressed as A.

A: A liquid film on a surface is broken after 5 seconds or more and less than 10 seconds.

B: A liquid film on a surface is broken after 1 second or more and less than 5 seconds.

C: A liquid film on a surface is instantly broken (less than 1 second).

<Lubricity>

The medical device manufactured in each Example was left to stand at room temperature for 24 hours or more in a storage container. The medical device was pulled up from the phosphate buffer solution in which the medical device was stationarily immersed, and subjected to sensory evaluation when rubbing with a human finger five times. The acceptable level is expressed as C or above.

A: There is extremely excellent lubricity (the finger slides to flow on a medical device surface and feel no resistance).

B: There is lubricity intermediate between A and C.

C: There is moderate lubricity (the finger slides on a medical device surface and hardly feels resistance).

D: Almost no lubricity (intermediate between C and E).

E: No lubricity (the finger does not easily slide on a medical device surface and feel large resistance).

<Moisture Content of Medical Device>

A medical device was immersed in a phosphate buffer solution and left to stand at room temperature for 24 hours or more. The medical device was pulled out from the phosphate buffer solution and, after wiping off the surface moisture with a wiping cloth ("Kimwipes" (registered trademark) manufactured by NIPPON PAPER CRECIA CO., LTD.), the mass (Ww) of the medical device was measured. Thereafter, the substrate was dried at 40° C. for 2 hours in a vacuum dryer and the mass (Wd) was measured. From these masses, the moisture content of the medical device was calculated in accordance with the following formula (1). Three measurements were taken of the moisture content, and the average of the measurements was regarded as the moisture content.

Moisture content (%) of medical device=100×($Ww$−$Wd$)/$Ww$     Formula (1)

<Friction Coefficient>

Under the following conditions, three measurements were taken of the friction coefficient of the medical device surface wetted with a phosphate buffer solution, and the average of the measurements was regarded as the friction coefficient. The acceptable level is 0.3 or less.

Apparatus: Friction tester KES-SE (manufactured by Kato Tech Co., Ltd.)
Friction SENS: H
  Measurement SPEED: 2×1 mm/sec
  Friction load: 44 g <Size>

Three measurements were taken of the diameter of a substrate having a contact lens shape, and the average of the measurements was regarded as the size.

<Total Light Transmittance>

The total light transmittance was measured using an SM color computer (Model SM-7-CH, manufactured by Suga Test Instruments Co., Ltd.). The central portion of the ophthalmic lens was cut out to a width of 5 mm, and water was lightly wiped off the lens, which was then used as a sample. ABC Digimatic Indicator (ID-C112, manufactured by Mitutoyo Corporation) was used to measure the thickness, and a sample having a thickness of 0.14 to 0.15 mm was used for measurement. A total light transmittance of 80% or more was regarded as an acceptable level.

<Molecular Weight Measurement>

The molecular weight of an internal wetting agent was measured under the following conditions.

Apparatus: Prominence GPC system manufactured by Shimadzu Corporation
Pump: LC-20AD
  Autosampler: SIL-20AHT
  Column oven: CTO-20A
Detector: RID-10A
  Column: GMPWXL manufactured by Tosoh Corporation (7.8 mm in inner diameter×30 cm, particle diameter of 13 µm)
  Solvent: water/methanol=1/1 (0.1 N lithium nitrate is added)
  Flow rate: 0.5 mL/minute
  Measurement time: 30 minutes
  Sample concentration: 0.1 to 0.3% by mass
  Sample injection amount: 100 µL
  Standard sample: Polyethylene oxide standard sample manufactured by Agilent Technologies, Inc. (0.1 kD to 1258 kD)

<Phosphate Buffer Solution>

Each composition of the phosphate buffer solutions used in the following Examples and Comparative Examples and the above-mentioned measurements is as follows.
KCl: 0.2 g/L
$KH_2PO_4$: 0.2 g/L
NaCl: 8.0 g/L
$Na_2HPO_4$ (anhydrous): 1.15 g/L
EDTA: 0.25 g/L Example 1

The formula (c) is as described below.

[Chemical Formula 2]

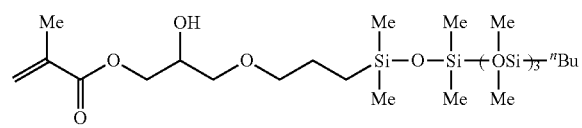

(c)

Preparations were made as follows: 38 parts by mass of silicone monomer represented by the above formula (c) (containing a hydroxyl group in an amount of 0.0017 equivalents/g); 2.0 parts by mass of acryl acid/N,N-dimethylacrylamide copolymer (copolymerized at a molar ratio of 1/9, having a molecular weight of 200,000, from Osaka Organic Chemical Industry Ltd.) as an internal wetting agent; 16 parts by mass of 2-ethylhexyl acrylate (from Tokyo Chemical Industry Co., Ltd.); 0.1 parts by mass of dimethylaminoethyl acrylate (from Kohjin Co., Ltd.); 41.9 parts by mass of 2-hydroxyethyl methacrylate (from Tokyo Chemical Industry Co., Ltd.); 2 parts by mass of triethylene glycol dimethacrylate (from Tokyo Chemical Industry Co., Ltd.); and with respect to the total mass of these materials, 5,000 ppm of light initiator IRGACURE (registered trademark) 819 (from Nagase & Co., Ltd.), 10,000 ppm of UV absorber (RUVA-93, from Otsuka Chemical Co., Ltd.), and 200 ppm of colorant (RB246, from Arran Chemical Company Ltd.). Furthermore, 40 parts by mass of t-amyl alcohol was prepared with respect to 100 parts by mass of the above-mentioned total mass. All these were mixed and stirred. A uniform transparent monomer mixture was obtained. This monomer mixture was degassed under an argon atmosphere, and then, the monomer mixture was filled into the gap between the molds having a lens shape under a nitrogen atmosphere in a glove box, and irradiated with light to be cured (using FL6D from Toshiba Corporation; at 8.4 kiloluxes; for 20 minutes) to obtain a medical device having a lens shape. The obtained medical device was immersed in an aqueous solution of 60% by mass of isopropanol (IPA) at 60° C. for 30 minutes to be removed from the molds, and then further immersed in an aqueous solution of 80% by mass of IPA at 60° C. for two hours to extract impurities such as remaining monomers. Then, the medical device was immersed in an aqueous solution of 50% by mass of IPA, an aqueous solution of 25% by mass of IPA, and then water for approximately 30 minutes each to be hydrated, wherein the IPA concentrations of these liquids were made different stepwise from higher to lower. Then, the medical device was immersed in a phosphate buffer solution in a 5-mL vial bottle, and the vial bottle was placed in an autoclave, in which the medical device was boiled at 120° C. for 30 minutes. The content ratio of silicon atoms with respect to the dry mass of the obtained medical device was 9.0% by mass. The results of evaluating the obtained medical device using the above methods are shown in Table 1.

Example 2

A medical device was produced in the same manner as in Example 1 except that 3.0 parts by mass of the internal wetting agent and 15 parts by mass of 2-ethylhexyl acrylate were used. The results of evaluating the obtained medical device using the above methods are shown in Table 1.

Example 3

A medical device was produced in the same manner as in Example 1 except that the internal wetting agent was changed to 2.0 parts by mass of an acryl acid/2-hydroxyethyl methacrylate/N,N-dimethylacrylamide copolymer (copolymerized at a molar ratio of 1/1/8; having a molecular weight of 500,000; from Osaka Organic Chemical Industry Ltd.). The results of evaluating the obtained medical device using the above methods are shown in Table 1.

Example 4

A medical device was produced in the same manner as in Example 3 except that 3.0 parts by mass of the internal wetting agent and 15 parts by mass of 2-ethylhexyl acrylate were used. The results of evaluating the obtained medical device using the above methods are shown in Table 1.

Example 5

A medical device was produced in the same manner as in Example 1 except that the internal wetting agent was changed to 3.0 parts by mass of an acryl acid/N,N-diethylacrylamide copolymer (copolymerized at a molar ratio of 1/9; having a molecular weight of 200,000; from Osaka Organic Chemical Industry Ltd.) and that 2-ethylhexyl acrylate was used in an amount of 15 parts by mass. The results of evaluating the obtained medical device using the above methods are shown in Table 1.

Example 6

A medical device was produced in the same manner as in Example 5 except that the internal wetting agent was changed to 3.0 parts by mass of an acryl acid/N,N-diethylacrylamide/N,N-dimethylacrylamide copolymer (copolymerized at a molar ratio of 1/1/8; having a molecular weight of 200,000; from Osaka Organic Chemical Industry Ltd.). The results of evaluating the obtained medical device using the above methods are shown in Table 1.

Comparative Example 1

A medical device was produced in the same manner as in Example 1 except that 0 parts by mass of the internal wetting agent and 18 parts by mass of 2-ethylhexyl acrylate were used. The results of evaluating the obtained medical device using the above methods are shown in Table 1. The results of the water wettability, lubricity, and friction coefficient were unacceptable.

Comparative Example 2

The formula (d) is as below-mentioned.

[Chemical Formula 3]

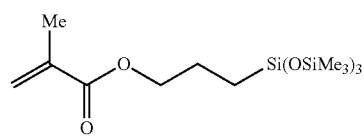

(d)

A medical device was produced in the same manner as in Example 1 except that 38 parts by mass of a silicone monomer (containing a hydroxyl group in an amount of 0 equivalents/g) represented by the formula (d), 0 parts by mass of the internal wetting agent, and 18 parts by mass of 2-ethylhexyl acrylate were used. The content ratio of silicon atoms with respect to the dry mass of the obtained medical device was 12.8% by mass. The obtained medical device was found to be so turbid that the turbidity could be visually observed. The results of evaluating the obtained medical device using the above methods are shown in Table 1. The results of the water wettability, lubricity, friction coefficient, and total light transmittance were unacceptable.

Comparative Example 3

The formula (e) is as below-mentioned.

[Chemical Formula 4]

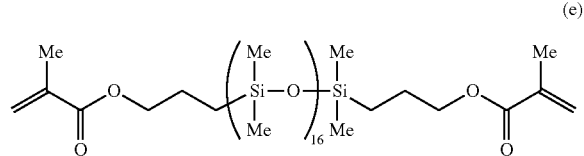

(e)

A medical device was produced in the same manner as in Example 1 except that 38 parts by mass of a silicone monomer (containing a hydroxyl group in an amount of 0 equivalents/g) represented by the formula (e), 0 parts by mass of the internal wetting agent, and 18 parts by mass of 2-ethylhexyl acrylate were used. The content ratio of silicon atoms with respect to the dry mass of the obtained medical device was 12.1% by mass. The obtained medical device was found to be so turbid that the turbidity could be visually observed. The results of evaluating the obtained medical device using the above methods are shown in Table 1. The results of the water wettability, lubricity, friction coefficient, and total light transmittance were unacceptable.

Comparative Example 4

An attempt was made to produce a medical device in the same manner as in Example 1 except that the internal wetting agent was changed to 3.0 parts by mass of a polyacryl acid "Sokalan (registered trademark) PA110S" (Mw: 250,000, manufactured by BASF SE) and that 2-ethylhexyl acrylate was used in an amount of 15 parts by mass, but the internal wetting agent was not dissolved in the mixture, failing to produce a medical device.

Comparative Example 5

An attempt was made to produce a medical device in the same manner as in Example 1 except that the internal wetting agent was changed to 3.0 parts by mass of an acryl acid/vinylpyrrolidone copolymer (copolymerized at a molar ratio of 1/4; having a molecular weight of 500,000; from Osaka Organic Chemical Industry Ltd.) and that 2-ethylhexyl acrylate was used in an amount of 15 parts by mass, but the internal wetting agent was not dissolved in the mixture, failing to produce a medical device.

Comparative Example 6

A medical device was produced in the same manner as in Example 1 except that 50 parts by mass of the silicone monomer, 0 parts by mass of the internal wetting agent, 7 parts by mass of 2-ethylhexyl acrylate, and 22 parts by mass of 2-hydroxyethyl methacrylate were used and that 19.9 parts by mass of N,N-dimethylacrylamide was newly added. The content ratio of silicon atoms with respect to the dry mass of the obtained medical device was 11.7% by mass. The results of evaluating the obtained medical device using the above methods are shown in Table 1. The results of the water wettability, lubricity, and friction coefficient were unacceptable.

Comparative Example 7

A medical device was produced in the same manner as in Example 1 except that the internal wetting agent was changed to 0.2 parts by mass of an acryl acid/vinylpyrrolidone/N,N-dimethylacrylamide copolymer (copolymerized at a molar ratio of 1/1/8; having a molecular weight of 370,000; from Osaka Organic Chemical Industry Ltd.) and that 2-hydroxyethyl methacrylate was used in an amount of 21.8 parts by mass. The obtained medical device was found to be so turbid that the turbidity could be visually observed. The results of evaluating the obtained medical device using the above methods are shown in Table 1. The results of the water wettability, lubricity, friction coefficient, and total light transmittance were unacceptable.

TABLE 1

| | | Example 1 | Example 2 | Example 3 | Example 4 | Example 5 | Example 6 | Comparative Example 1 |
|---|---|---|---|---|---|---|---|---|
| Composition (parts by mass) | Internal Wetting Agent | 2 | 3 | 2 | 3 | 3 | 3 | 0 |
| | Silicone Component Formula (c) | 38 | 38 | 38 | 38 | 38 | 38 | 38 |
| | Silicone Component Formula (d) | 0 | 0 | 0 | 0 | 0 | 0 | 0 |
| | Silicone Component Formula (e) | 0 | 0 | 0 | 0 | 0 | 0 | 0 |
| | 2-Ethylhexyl Acrylate | 16 | 15 | 16 | 15 | 15 | 15 | 18 |
| | Dimethylaminoethyl Acrylate | 0.1 | 0.1 | 0.1 | 0.1 | 0.1 | 0.1 | 0.1 |
| | 2-Hydroxyethyl Methacrylate | 41.9 | 41.9 | 41.9 | 41.9 | 41.9 | 41.9 | 41.9 |
| | N,N-Dimethylacrylamide | 0 | 0 | 0 | 0 | 0 | 0 | 0 |
| | Triethylene Glycol Dimethacrylate | 2 | 2 | 2 | 2 | 2 | 2 | 2 |
| | Photoinitiator | 0.5 | 0.5 | 0.5 | 0.5 | 0.5 | 0.5 | 0.5 |
| | UV Absorber | 1 | 1 | 1 | 1 | 1 | 1 | 1 |
| | Colorant | 0.02 | 0.02 | 0.02 | 0.02 | 0.02 | 0.02 | 0.02 |
| | t-Amyl Alcohol | 40 | 40 | 40 | 40 | 40 | 40 | 40 |
| Evaluation Results | Water Wettability | A (5 seconds) | A (5 seconds) | A (5 seconds) | A (5 seconds) | A (5 seconds) | A (5 seconds) | C (0 seconds) |
| | Lubricity | C | C | C | B | B | B | E |
| | Moisture Content (%) | 18.0 | 22.6 | 18.9 | 21.0 | 21.5 | 21.9 | 9.2 |
| | Friction Coefficient | 0.164 | 0.163 | 0.111 | 0.089 | 0.085 | 0.090 | 0.736 |
| | Size (mm) | 13.0 | 13.3 | 12.9 | 13.2 | 13.3 | 13.2 | 12.3 |
| | Total Light Transmittance (%) | 88.6 | 88.7 | 88.9 | 88.8 | 88.5 | 88.1 | 85.5 |

| | | Comparative Example 2 | Comparative Example 3 | Comparative Example 4 | Comparative Example 5 | Comparative Example 6 | Comparative Example 7 |
|---|---|---|---|---|---|---|---|
| Composition (parts by mass) | Internal Wetting Agent | 0 | 0 | 3 | 3 | 0 | 0.2 |
| | Silicone Component Formula (c) | 0 | 0 | 38 | 38 | 50 | 50 |

TABLE 1-continued

|  |  |  |  |  |  |  |  |
|---|---|---|---|---|---|---|---|
|  | Silicone Component Formula (d) | 38 | 0 | 0 | 0 | 0 | 0 |
|  | Silicone Component Formula (e) | 0 | 38 | 0 | 0 | 0 | 0 |
|  | 2-Ethylhexyl Acrylate | 18 | 18 | 15 | 15 | 7 | 7 |
|  | Dimethylaminoethyl Acrylate | 0.1 | 0.1 | 0.1 | 0.1 | 0.1 | 0.1 |
|  | 2-Hydroxyethyl Methacrylate | 41.9 | 41.9 | 41.9 | 41.9 | 22 | 21.8 |
|  | N,N-Dimethylacrylamide | 0 | 0 | 0 | 0 | 19.9 | 19.9 |
|  | Triethylene Glycol Dimethacrylate | 2 | 2 | 2 | 2 | 2 | 2 |
|  | Photoinitiator | 0.5 | 0.5 | 0.5 | 0.5 | 0.5 | 0.5 |
|  | UV Absorber | 1 | 1 | 1 | 1 | 1 | 1 |
|  | Colorant | 0.02 | 0.02 | 0.02 | 0.02 | 0.02 | 0.02 |
|  | t-Amyl Alcohol | 40 | 40 | 40 | 40 | 40 | 40 |
| Evaluation Results | Water Wettability | C (0 seconds) | C (0 seconds) | — | — | C (0 seconds) | C (0 seconds) |
|  | Lubricity | E | E | — | — | E | E |
|  | Moisture Content (%) | 10.0 | 10.1 | — | — | 14.1 | 14.2 |
|  | Friction Coefficient | 0.751 | 0.768 | — | — | 0.805 | 0.810 |
|  | Size (mm) | 12.2 | 12.3 | — | — | 12.3 | 12.4 |
|  | Total Light Transmittance (%) | 60.0 | 47.0 | — | — | 83.0 | 50.0 |

The invention claimed is:

1. A medical device comprising an internal wetting agent and a silicone copolymer wherein:
   (1) said internal wetting agent contains a copolymer of an open-chain compound having an acidic group and an open-chain compound having an amide group;
   wherein
   the copolymer is a copolymer containing, as monomer units, a chain compound having an acidic group and a chain compound having an amide group,
   the chain compound having an acidic group is selected from a group consisting of methacrylic acids, acrylic acids and salts thereof,
   the chain compound having an amide group is N,N-diethylacrylamide, and
   the copolymerization ratio of [mass of monomer units having an acidic group]/[mass of monomer units having an amide group] is 1/99 to 70/30,
   (2) said internal wetting agent is contained in the range of from 0.1 to 10% by mass with respect to the whole medical device;
   (3) said silicone copolymer is formed from a first monomer having silicone and hydroxyl groups, and a second monomer having an alkyl (meth)acrylate group,
   wherein the content ratio of said hydroxyl group in the first monomer is in the range of from 0.0005 to 0.01 equivalents/g, and
   wherein the amount of the second monomer is 0.1% by mass to 30% by mass with respect to the whole medical device.

2. The medical device according to claim 1, which contains silicon atoms at a ratio in the range of from 5 to 30% by mass with respect to the dry mass of said medical device.

3. The medical device according to claim 1, wherein said copolymer of a silicone monomer is a copolymer of a silicone monomer having a hydroxyl group and a (meth)acryloyl group-containing monomer.

4. The medical device according to claim 3, wherein said (meth)acryloyl group-containing monomer is hydroxyalkyl (meth)acrylate.

5. The medical device according to claim 4, wherein said hydroxyalkyl (meth)acrylate is 2-hydroxyethyl (meth)acrylate.

6. The medical device according to claim 1, which is an ophthalmic lens, a dermal covering material, a wound dressing material, a skin protection material, a skin medicine carrier, an infusion tube, a gas delivery tube, a drainage tube, a blood circuit, a covering tube, a catheter, a stent, a sheath, a biosensor chip, or an endoscopic covering material.

7. The medical device according to claim 6, wherein said ophthalmic lens is a contact lens.

8. The medical device according to claim 1, wherein the copolymerization ratio of [mass of monomer units having an acidic group]/[mass of monomer units having an amide group] is 5/99 to 30/70 and the internal wetting agent has a mass average molecular weight of 100,000 to 700,000.

* * * * *